(12) United States Patent
Collins et al.

(10) Patent No.: US 8,512,332 B2
(45) Date of Patent: Aug. 20, 2013

(54) REAL-TIME ARC CONTROL IN ELECTROSURGICAL GENERATORS

(75) Inventors: George J. Collins, Fort Collins, CO (US); Cameron A. Moore, Loveland, CO (US); Arlen K. Ward, Thornton, CO (US)

(73) Assignees: Covidien LP, Mansfield, MA (US); Colorado State University Research Foundation, Fort Collins, CO (US)

( * ) Notice: Subject to any disclaimer, the term of this patent is extended or adjusted under 35 U.S.C. 154(b) by 1733 days.

(21) Appl. No.: 11/859,039

(22) Filed: Sep. 21, 2007

(65) Prior Publication Data

US 2009/0082765 A1    Mar. 26, 2009

(51) Int. Cl.
*A61B 18/18* (2006.01)

(52) U.S. Cl.
USPC .......................................................... 606/38

(58) Field of Classification Search
USPC .................................................... 606/32–52
See application file for complete search history.

(56) References Cited

U.S. PATENT DOCUMENTS

| | | | |
|---|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | E. Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

European Search Report for European Application No: 11186103.5 dated Sep. 7, 2012.

(Continued)

*Primary Examiner* — Michael Peffley
*Assistant Examiner* — Ronald Hupczey, Jr.

(57) ABSTRACT

An electrosurgical generator is disclosed. The generator includes a radio frequency output stage configured to generate a radio frequency waveform and a sensor circuit configured to measure a property of the radio frequency waveform during a predetermined sampling period to determine whether an arc event has occurred. The generator also includes a controller configured to determine a total charge and/or total energy deposited by the radio frequency waveform during the predetermined sampling period associated with the arc event. The controller is further configured to adjust the output of the electrosurgical generator based on at least one parameter to limit arcing.

10 Claims, 3 Drawing Sheets

(56) References Cited

U.S. PATENT DOCUMENTS

| | | | |
|---|---|---|---|
| 3,486,115 | A | 12/1969 | Anderson |
| 3,495,584 | A | 2/1970 | Schwalm |
| 3,513,353 | A | 5/1970 | Lansch |
| 3,514,689 | A | 5/1970 | Giannamore |
| 3,515,943 | A | 6/1970 | Warrington |
| 3,551,786 | A | 12/1970 | Van Gulik |
| 3,562,623 | A | 2/1971 | Farnsworth |
| 3,571,644 | A | 3/1971 | Jakoubovitch |
| 3,589,363 | A | 6/1971 | Banko |
| 3,595,221 | A | 7/1971 | Blackett |
| 3,601,126 | A | 8/1971 | Estes |
| 3,611,053 | A | 10/1971 | Rowell |
| 3,641,422 | A | 2/1972 | Farnsworth et al. |
| 3,642,008 | A | 2/1972 | Bolduc |
| 3,662,151 | A | 5/1972 | Haffey |
| 3,675,655 | A | 7/1972 | Sittner |
| 3,683,923 | A | 8/1972 | Anderson |
| 3,693,613 | A | 9/1972 | Kelman |
| 3,697,808 | A | 10/1972 | Lee |
| 3,699,967 | A | 10/1972 | Anderson |
| 3,720,896 | A | 3/1973 | Bierlein |
| 3,743,918 | A | 7/1973 | Maitre |
| 3,766,434 | A | 10/1973 | Sherman |
| 3,768,482 | A | 10/1973 | Shaw |
| 3,801,766 | A | 4/1974 | Morrison, Jr. |
| 3,801,800 | A | 4/1974 | Newton |
| 3,812,858 | A | 5/1974 | Oringer |
| 3,815,015 | A | 6/1974 | Swin et al. |
| 3,826,263 | A | 7/1974 | Cage et al. |
| 3,848,600 | A | 11/1974 | Patrick, Jr. et al. |
| 3,870,047 | A | 3/1975 | Gonser |
| 3,875,945 | A | 4/1975 | Friedman |
| 3,885,569 | A | 5/1975 | Judson |
| 3,897,787 | A | 8/1975 | Ikuno et al. |
| 3,897,788 | A | 8/1975 | Newton |
| 3,898,554 | A | 8/1975 | Knudsen |
| 3,905,373 | A | 9/1975 | Gonser |
| 3,913,583 | A | 10/1975 | Bross |
| 3,923,063 | A | 12/1975 | Andrews et al. |
| 3,933,157 | A | 1/1976 | Bjurwill et al. |
| 3,946,738 | A | 3/1976 | Newton et al. |
| 3,952,748 | A | 4/1976 | Kaliher et al. |
| 3,963,030 | A | 6/1976 | Newton |
| 3,964,487 | A | 6/1976 | Judson |
| 3,971,365 | A | 7/1976 | Smith |
| 3,978,393 | A | 8/1976 | Wisner et al. |
| 3,980,085 | A | 9/1976 | Ikuno |
| 4,005,714 | A | 2/1977 | Hilebrandt |
| 4,024,467 | A | 5/1977 | Andrews et al. |
| 4,041,952 | A | 8/1977 | Morrison, Jr. et al. |
| 4,051,855 | A | 10/1977 | Schneiderman |
| 4,074,719 | A | 2/1978 | Semm |
| 4,092,986 | A | 6/1978 | Schneiderman |
| 4,094,320 | A | 6/1978 | Newton et al. |
| 4,097,773 | A | 6/1978 | Lindmark |
| 4,102,341 | A | 7/1978 | Ikuno et al. |
| 4,114,623 | A | 9/1978 | Meinke et al. |
| 4,121,590 | A | 10/1978 | Gonser |
| 4,123,673 | A | 10/1978 | Gonser |
| 4,126,137 | A | 11/1978 | Archibald |
| 4,171,700 | A | 10/1979 | Farin |
| 4,188,927 | A | 2/1980 | Harris |
| 4,191,188 | A | 3/1980 | Belt et al. |
| 4,196,734 | A | 4/1980 | Harris |
| 4,200,104 | A | 4/1980 | Harris |
| 4,200,105 | A | 4/1980 | Gonser |
| 4,209,018 | A | 6/1980 | Meinke et al. |
| 4,231,372 | A | 11/1980 | Newton |
| 4,232,676 | A | 11/1980 | Herczog |
| 4,237,887 | A | 12/1980 | Gonser |
| 4,281,373 | A | 7/1981 | Mabille |
| 4,287,557 | A | 9/1981 | Brehse |
| 4,296,413 | A | 10/1981 | Milkovic |
| 4,303,073 | A | 12/1981 | Archibald |
| 4,311,154 | A | 1/1982 | Sterzer et al. |
| 4,314,559 | A | 2/1982 | Allen |
| 4,321,926 | A | 3/1982 | Roge |
| 4,334,539 | A | 6/1982 | Childs et al. |
| 4,343,308 | A | 8/1982 | Gross |
| 4,372,315 | A | 2/1983 | Shapiro et al. |
| 4,376,263 | A | 3/1983 | Pittroff et al. |
| 4,378,801 | A | 4/1983 | Oosten |
| 4,384,582 | A | 5/1983 | Watt |
| 4,397,314 | A | 8/1983 | Vaguine |
| 4,411,266 | A | 10/1983 | Cosman |
| 4,416,276 | A | 11/1983 | Newton et al. |
| 4,416,277 | A | 11/1983 | Newton et al. |
| 4,429,694 | A | 2/1984 | McGreevy |
| 4,436,091 | A | 3/1984 | Banko |
| 4,437,464 | A | 3/1984 | Crow |
| 4,438,766 | A | 3/1984 | Bowers |
| 4,463,759 | A | 8/1984 | Garito et al. |
| 4,472,661 | A | 9/1984 | Culver |
| 4,474,179 | A | 10/1984 | Koch |
| 4,492,231 | A | 1/1985 | Auth |
| 4,492,832 | A | 1/1985 | Taylor |
| 4,494,541 | A | 1/1985 | Archibald |
| 4,514,619 | A | 4/1985 | Kugelman |
| 4,520,818 | A | 6/1985 | Mickiewicz |
| 4,559,496 | A | 12/1985 | Harnden, Jr. et al. |
| 4,559,943 | A | 12/1985 | Bowers |
| 4,565,200 | A | 1/1986 | Cosman |
| 4,566,454 | A | 1/1986 | Mehl et al. |
| 4,569,345 | A | 2/1986 | Manes |
| 4,582,057 | A | 4/1986 | Auth et al. |
| 4,586,120 | A | 4/1986 | Malik et al. |
| 4,590,934 | A | 5/1986 | Malis et al. |
| 4,595,248 | A | 6/1986 | Brown |
| 4,608,977 | A | 9/1986 | Brown |
| 4,615,330 | A | 10/1986 | Nagasaki et al. |
| 4,630,218 | A | 12/1986 | Hurley |
| 4,632,109 | A | 12/1986 | Paterson |
| 4,644,955 | A | 2/1987 | Mioduski |
| 4,651,264 | A | 3/1987 | Shiao-Chung Hu |
| 4,651,280 | A | 3/1987 | Chang et al. |
| 4,657,015 | A | 4/1987 | Irnich |
| 4,658,815 | A | 4/1987 | Farin et al. |
| 4,658,819 | A | 4/1987 | Harris et al. |
| 4,658,820 | A | 4/1987 | Klicek |
| 4,662,383 | A | 5/1987 | Sogawa et al. |
| 4,691,703 | A | 9/1987 | Auth et al. |
| 4,727,874 | A | 3/1988 | Bowers et al. |
| 4,735,204 | A | 4/1988 | Sussman et al. |
| 4,739,759 | A | 4/1988 | Rexroth et al. |
| 4,741,334 | A | 5/1988 | Irnich |
| 4,754,757 | A | 7/1988 | Feucht |
| 4,767,999 | A | 8/1988 | VerPlanck |
| 4,768,969 | A | 9/1988 | Bauer et al. |
| 4,788,634 | A | 11/1988 | Schlecht et al. |
| 4,805,621 | A | 2/1989 | Heinze et al. |
| 4,818,954 | A | 4/1989 | Flachenecker et al. |
| 4,827,927 | A | 5/1989 | Newton |
| 4,848,335 | A | 7/1989 | Manes |
| 4,860,745 | A | 8/1989 | Farin et al. |
| 4,862,889 | A | 9/1989 | Feucht |
| 4,887,199 | A | 12/1989 | Whittle |
| 4,890,610 | A | 1/1990 | Kirwan et al. |
| 4,903,696 | A | 2/1990 | Stasz et al. |
| 4,907,589 | A | 3/1990 | Cosman |
| 4,922,210 | A | 5/1990 | Flachenecker et al. |
| 4,931,047 | A | 6/1990 | Broadwin et al. |
| 4,931,717 | A | 6/1990 | Gray et al. |
| 4,938,761 | A | 7/1990 | Ensslin |
| 4,942,313 | A | 7/1990 | Kinzel |
| 4,959,606 | A | 9/1990 | Forge |
| 4,961,047 | A | 10/1990 | Carder |
| 4,961,435 | A | 10/1990 | Kitagawa et al. |
| 4,966,597 | A | 10/1990 | Cosman |
| 4,969,885 | A | 11/1990 | Farin |
| 4,992,719 | A | 2/1991 | Harvey |
| 4,993,430 | A | 2/1991 | Shimoyama et al. |
| 4,995,877 | A | 2/1991 | Ams et al. |
| 5,015,227 | A | 5/1991 | Broadwin et al. |
| 5,024,668 | A | 6/1991 | Peters et al. |

| | | |
|---|---|---|
| 5,044,977 A | 9/1991 | Vindigni |
| 5,067,953 A | 11/1991 | Feucht |
| 5,075,839 A | 12/1991 | Fisher et al. |
| 5,087,257 A | 2/1992 | Farin |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker |
| 5,119,284 A | 6/1992 | Fisher et al. |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,161,893 A | 11/1992 | Shigezawa et al. |
| 5,167,658 A | 12/1992 | Ensslin |
| 5,167,659 A | 12/1992 | Ohtomo et al. |
| 5,190,517 A | 3/1993 | Zieve et al. |
| 5,196,008 A | 3/1993 | Kuenecke |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,234,427 A | 8/1993 | Ohtomo et al. |
| 5,249,121 A | 9/1993 | Baum et al. |
| 5,249,585 A | 10/1993 | Turner et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin |
| 5,281,213 A | 1/1994 | Milder et al. |
| 5,282,840 A | 2/1994 | Hudrlik |
| 5,290,283 A | 3/1994 | Suda |
| 5,295,857 A | 3/1994 | Toly |
| 5,300,068 A | 4/1994 | Rosar et al. |
| 5,300,070 A | 4/1994 | Gentelia |
| 5,304,917 A | 4/1994 | Somerville |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman |
| 5,342,357 A | 8/1994 | Nardella |
| 5,342,409 A | 8/1994 | Mullett |
| 5,346,406 A | 9/1994 | Hoffman et al. |
| 5,346,491 A | 9/1994 | Oertli |
| 5,348,554 A | 9/1994 | Imran et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson |
| 5,383,876 A | 1/1995 | Nardella |
| 5,383,917 A | 1/1995 | Desai et al. |
| 5,385,148 A | 1/1995 | Lesh et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,422,926 A | 6/1995 | Smith et al. |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,425,704 A | 6/1995 | Sakurai et al. |
| 5,429,596 A | 7/1995 | Arias et al. |
| 5,430,434 A | 7/1995 | Lederer et al. |
| 5,432,459 A | 7/1995 | Thompson |
| 5,433,739 A | 7/1995 | Sluijter et al. |
| 5,436,566 A | 7/1995 | Thompson |
| 5,438,302 A | 8/1995 | Goble |
| 5,443,463 A | 8/1995 | Stern et al. |
| 5,445,635 A | 8/1995 | Denen |
| 5,451,224 A | 9/1995 | Goble et al. |
| 5,452,725 A | 9/1995 | Martenson |
| 5,454,809 A | 10/1995 | Janssen |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,474,464 A | 12/1995 | Drewnicki |
| 5,480,399 A | 1/1996 | Hebborn |
| 5,483,952 A | 1/1996 | Aranyi |
| 5,496,312 A | 3/1996 | Klicek |
| 5,496,313 A | 3/1996 | Gentelia et al. |
| 5,496,314 A | 3/1996 | Eggers |
| 5,500,012 A | 3/1996 | Brucker et al. |
| 5,500,616 A | 3/1996 | Ochi |
| 5,511,993 A | 4/1996 | Yamada et al. |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa |
| 5,540,684 A | 7/1996 | Hassler, Jr. |
| 5,541,376 A | 7/1996 | Ladtkow et al. |
| 5,545,161 A | 8/1996 | Imran |
| 5,556,396 A | 9/1996 | Cohen et al. |
| 5,558,671 A | 9/1996 | Yates |
| 5,562,720 A | 10/1996 | Stern et al. |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |
| 5,693,042 A | 12/1997 | Boiarski et al. |
| 5,693,078 A | 12/1997 | Desai et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |

| | | | | | |
|---|---|---|---|---|---|
| 5,729,448 A | 3/1998 | Haynie et al. | 6,059,781 A | 5/2000 | Yamanashi et al. |
| 5,733,281 A | 3/1998 | Nardella | 6,063,075 A | 5/2000 | Mihori |
| 5,735,846 A | 4/1998 | Panescu et al. | 6,063,078 A | 5/2000 | Wittkampf |
| 5,738,683 A | 4/1998 | Osypka | 6,066,137 A | 5/2000 | Greep |
| 5,743,900 A | 4/1998 | Hara | 6,068,627 A | 5/2000 | Orszulak et al. |
| 5,743,903 A | 4/1998 | Stern et al. | 6,074,089 A | 6/2000 | Hollander et al. |
| 5,749,869 A | 5/1998 | Lindenmeier et al. | 6,074,386 A | 6/2000 | Goble et al. |
| 5,749,871 A | 5/1998 | Hood et al. | 6,074,388 A | 6/2000 | Tockweiler et al. |
| 5,755,715 A | 5/1998 | Stern | 6,080,149 A | 6/2000 | Huang et al. |
| 5,766,153 A | 6/1998 | Eggers et al. | 6,088,614 A | 7/2000 | Swanson |
| 5,766,165 A | 6/1998 | Gentelia et al. | 6,093,186 A | 7/2000 | Goble |
| 5,769,847 A | 6/1998 | Panescu | 6,102,497 A | 8/2000 | Ehr et al. |
| 5,772,659 A | 6/1998 | Becker et al. | 6,102,907 A | 8/2000 | Smethers et al. |
| 5,788,688 A | 8/1998 | Bauer et al. | 6,113,591 A | 9/2000 | Whayne et al. |
| 5,792,138 A | 8/1998 | Shipp | 6,113,592 A | 9/2000 | Taylor |
| 5,797,902 A | 8/1998 | Netherly | 6,113,593 A | 9/2000 | Tu et al. |
| 5,807,253 A | 9/1998 | Dumoulin et al. | 6,113,596 A | 9/2000 | Hooven |
| 5,810,804 A | 9/1998 | Gough et al. | 6,123,701 A | 9/2000 | Nezhat |
| 5,814,092 A | 9/1998 | King | 6,123,702 A | 9/2000 | Swanson et al. |
| 5,817,091 A | 10/1998 | Nardella et al. | 6,132,429 A | 10/2000 | Baker |
| 5,817,093 A | 10/1998 | Williamson, IV et al. | 6,142,992 A | 11/2000 | Cheng et al. |
| 5,820,568 A | 10/1998 | Willis | 6,155,975 A | 12/2000 | Urich et al. |
| 5,830,212 A | 11/1998 | Cartmell | 6,162,184 A | 12/2000 | Swanson et al. |
| 5,836,909 A | 11/1998 | Cosmescu | 6,162,217 A | 12/2000 | Kannenberg et al. |
| 5,836,943 A | 11/1998 | Miller, III | 6,165,169 A | 12/2000 | Panescu et al. |
| 5,836,990 A | 11/1998 | Li | 6,171,304 B1 | 1/2001 | Netherly et al. |
| 5,827,271 A | 12/1998 | Bussey et al. | 6,183,468 B1 | 2/2001 | Swanson et al. |
| 5,843,019 A | 12/1998 | Eggers et al. | 6,186,147 B1 | 2/2001 | Cobb |
| 5,843,075 A | 12/1998 | Taylor | 6,188,211 B1 | 2/2001 | Rincon-Mora et al. |
| 5,846,236 A | 12/1998 | Lindenmeier et al. | 6,193,713 B1 | 2/2001 | Geistert et al. |
| 5,849,010 A | 12/1998 | Wurzer et al. | 6,197,023 B1 | 3/2001 | Muntermann |
| 5,853,409 A | 12/1998 | Swanson et al. | 6,203,541 B1 | 3/2001 | Keppel |
| 5,860,832 A | 1/1999 | Wayt et al. | 6,210,403 B1 * | 4/2001 | Klicek .......................... 606/34 |
| 5,865,788 A | 2/1999 | Edwards et al. | 6,216,704 B1 | 4/2001 | Ingle et al. |
| 5,868,737 A | 2/1999 | Taylor et al. | 6,222,356 B1 | 4/2001 | Taghizadeh-Kaschani |
| 5,868,739 A | 2/1999 | Lindenmeier et al. | 6,228,078 B1 | 5/2001 | Eggers et al. |
| 5,868,740 A | 2/1999 | LeVeen et al. | 6,228,080 B1 | 5/2001 | Gines |
| 5,871,481 A | 2/1999 | Kannenberg et al. | 6,228,081 B1 | 5/2001 | Goble |
| 5,891,142 A | 4/1999 | Eggers et al. | 6,231,569 B1 | 5/2001 | Bek |
| 5,897,552 A | 4/1999 | Edwards et al. | 6,232,556 B1 | 5/2001 | Daugherty et al. |
| 5,906,614 A | 5/1999 | Stern et al. | 6,235,020 B1 | 5/2001 | Cheng et al. |
| 5,908,444 A | 6/1999 | Azure | 6,235,022 B1 | 5/2001 | Hallock et al. |
| 5,913,882 A | 6/1999 | King | 6,237,604 B1 | 5/2001 | Burnside et al. |
| 5,921,982 A | 7/1999 | Lesh et al. | 6,238,387 B1 | 5/2001 | Miller, III |
| 5,925,070 A | 7/1999 | King et al. | 6,238,388 B1 | 5/2001 | Ellman |
| 5,931,836 A | 8/1999 | Hatta et al. | 6,241,723 B1 | 6/2001 | Heim et al. |
| 5,938,690 A | 8/1999 | Law et al. | 6,241,725 B1 | 6/2001 | Cosman |
| 5,944,553 A | 8/1999 | Yasui et al. | 6,243,654 B1 | 6/2001 | Johnson et al. |
| 5,948,007 A | 9/1999 | Starkebaum et al. | 6,245,061 B1 | 6/2001 | Panescu et al. |
| 5,951,545 A | 9/1999 | Schilling | 6,245,063 B1 | 6/2001 | Uphoff |
| 5,951,546 A | 9/1999 | Lorentzen | 6,245,065 B1 | 6/2001 | Panescu |
| 5,954,686 A | 9/1999 | Garito et al. | 6,246,912 B1 | 6/2001 | Sluijter et al. |
| 5,954,717 A | 9/1999 | Behl et al. | 6,251,106 B1 | 6/2001 | Becker et al. |
| 5,954,719 A | 9/1999 | Chen et al. | 6,254,422 B1 | 7/2001 | Feye-Hohmann |
| 5,957,961 A | 9/1999 | Maguire et al. | 6,258,085 B1 | 7/2001 | Eggleston |
| 5,959,253 A | 9/1999 | Shinchi | 6,261,285 B1 | 7/2001 | Novak |
| 5,961,344 A | 10/1999 | Rosales et al. | 6,261,286 B1 | 7/2001 | Goble et al. |
| 5,964,746 A | 10/1999 | McCary | 6,267,760 B1 | 7/2001 | Swanson |
| 5,971,980 A | 10/1999 | Sherman | 6,273,886 B1 | 8/2001 | Edwards |
| 5,971,981 A | 10/1999 | Hill et al. | 6,275,786 B1 | 8/2001 | Daners |
| 5,976,128 A | 11/1999 | Schilling et al. | 6,293,941 B1 | 9/2001 | Strul |
| 5,983,141 A | 11/1999 | Sluijter et al. | 6,293,942 B1 | 9/2001 | Goble et al. |
| 6,007,532 A | 12/1999 | Netherly | 6,293,943 B1 | 9/2001 | Panescu et al. |
| 6,010,499 A | 1/2000 | Cobb | 6,296,636 B1 | 10/2001 | Cheng et al. |
| 6,013,074 A | 1/2000 | Taylor | 6,306,131 B1 | 10/2001 | Hareyama et al. |
| 6,014,581 A | 1/2000 | Whayne et al. | 6,306,134 B1 | 10/2001 | Goble et al. |
| 6,017,338 A | 1/2000 | Brucker et al. | 6,309,386 B1 | 10/2001 | Bek |
| 6,022,346 A | 2/2000 | Panescu et al. | 6,322,558 B1 | 11/2001 | Taylor et al. |
| 6,022,347 A | 2/2000 | Lindenmeier et al. | 6,325,799 B1 | 12/2001 | Goble |
| 6,033,399 A | 3/2000 | Gines | 6,337,998 B1 | 1/2002 | Behl et al. |
| 6,039,731 A | 3/2000 | Taylor et al. | 6,338,657 B1 | 1/2002 | Harper et al. |
| 6,039,732 A | 3/2000 | Ichikawa et al. | 6,350,262 B1 | 2/2002 | Ashley |
| 6,041,260 A | 3/2000 | Stern et al. | 6,358,245 B1 | 3/2002 | Edwards |
| 6,044,283 A | 3/2000 | Fein et al. | 6,364,877 B1 | 4/2002 | Goble et al. |
| 6,053,910 A | 4/2000 | Fleenor | 6,371,963 B1 | 4/2002 | Nishtala et al. |
| 6,053,912 A | 4/2000 | Panescu et al. | 6,383,183 B1 | 5/2002 | Sekino et al. |
| 6,055,458 A | 4/2000 | Cochran et al. | 6,391,024 B1 | 5/2002 | Sun et al. |
| 6,056,745 A | 5/2000 | Panescu et al. | 6,398,779 B1 | 6/2002 | Buysse et al. |
| 6,056,746 A | 5/2000 | Goble et al. | 6,398,781 B1 | 6/2002 | Goble et al. |

| Patent No. | Date | Inventor(s) |
|---|---|---|
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,722 B1 | 6/2002 | Hoey et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,426,886 B1 | 7/2002 | Goder |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock |
| 6,458,122 B1 | 10/2002 | Pozzato |
| 6,464,689 B1 | 10/2002 | Qin |
| 6,464,696 B1 | 10/2002 | Oyama |
| 6,468,270 B1 | 10/2002 | Hovda et al. |
| 6,468,273 B1 | 10/2002 | Leveen et al. |
| 6,482,201 B1 | 11/2002 | Olsen et al. |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,260 B1 | 4/2003 | Markel et al. |
| 6,546,270 B1 | 4/2003 | Goldin et al. |
| 6,547,786 B1 * | 4/2003 | Goble ............................ 606/34 |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai et al. |
| 6,626,901 B1 | 9/2003 | Treat et al. |
| 6,629,973 B1 | 10/2003 | Wardell et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 * | 2/2004 | Heim et al. ................... 606/34 |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,783,523 B2 | 8/2004 | Qin |
| 6,784,405 B2 | 8/2004 | Flugstad et al. |
| 6,786,905 B2 | 9/2004 | Swanson et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,824,539 B2 | 11/2004 | Novak |
| 6,830,569 B2 | 12/2004 | Thompson |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,958,064 B2 | 10/2005 | Rioux et al. |
| 6,962,587 B2 | 11/2005 | Johnson et al. |
| 6,966,907 B2 | 11/2005 | Goble |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,094,231 B1 | 8/2006 | Ellman et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |

| Patent No. | Date | Name |
|---|---|---|
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,195,627 B2 | 3/2007 | Amoah et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 * | 11/2007 | Wham et al. .......... 606/34 |
| 7,300,437 B2 | 11/2007 | Pozzato |
| 7,303,557 B2 | 12/2007 | Wham et al. |
| 7,305,311 B2 | 12/2007 | Van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,479,140 B2 | 1/2009 | Ellman et al. |
| 7,491,199 B2 | 2/2009 | Goble |
| 7,491,201 B2 | 2/2009 | Shields et al. |
| 7,513,896 B2 | 4/2009 | Orszulak |
| 7,525,398 B2 | 4/2009 | Nishimura et al. |
| 2001/0014804 A1 | 8/2001 | Goble et al. |
| 2001/0029315 A1 | 10/2001 | Sakurai et al. |
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0052599 A1 | 5/2002 | Goble |
| 2002/0068932 A1 | 6/2002 | Edwards |
| 2002/0107517 A1 | 8/2002 | Witt et al. |
| 2002/0111624 A1 | 8/2002 | Witt et al. |
| 2002/0151889 A1 | 10/2002 | Swanson et al. |
| 2002/0193787 A1 | 12/2002 | Qin |
| 2003/0004510 A1 | 1/2003 | Wham et al. |
| 2003/0060818 A1 | 3/2003 | Kannenberg |
| 2003/0078572 A1 | 4/2003 | Pearson et al. |
| 2003/0139741 A1 | 7/2003 | Goble et al. |
| 2003/0153908 A1 | 8/2003 | Goble |
| 2003/0163123 A1 | 8/2003 | Goble |
| 2003/0163124 A1 | 8/2003 | Goble |
| 2003/0171745 A1 | 9/2003 | Francischelli |
| 2003/0181898 A1 | 9/2003 | Bowers |
| 2003/0199863 A1 | 10/2003 | Swanson |
| 2003/0225401 A1 | 12/2003 | Eggers et al. |
| 2004/0002745 A1 | 1/2004 | Fleming |
| 2004/0015159 A1 | 1/2004 | Slater et al. |
| 2004/0015163 A1 | 1/2004 | Buysse et al. |
| 2004/0015216 A1 | 1/2004 | DeSisto |
| 2004/0019347 A1 | 1/2004 | Sakurai |
| 2004/0024395 A1 | 2/2004 | Ellman |
| 2004/0030328 A1 | 2/2004 | Eggers |
| 2004/0030330 A1 | 2/2004 | Brassell et al. |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0167508 A1 | 8/2004 | Wham et al. |
| 2004/0172016 A1 | 9/2004 | Bek |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble |
| 2005/0004564 A1 | 1/2005 | Wham |
| 2005/0004569 A1 | 1/2005 | Witt et al. |
| 2005/0004634 A1 | 1/2005 | Ricart et al. |
| 2005/0021020 A1 | 1/2005 | Blaha et al. |
| 2005/0021022 A1 | 1/2005 | Sturm et al. |
| 2005/0101949 A1 | 5/2005 | Harano et al. |
| 2005/0101951 A1 | 5/2005 | Wham |
| 2005/0109111 A1 | 5/2005 | Manlove et al. |
| 2005/0113818 A1 | 5/2005 | Sartor |
| 2005/0113819 A1 | 5/2005 | Wham |
| 2005/0149151 A1 | 7/2005 | Orszulak |
| 2005/0182398 A1 | 8/2005 | Paterson |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 * | 10/2006 | Behnke et al. .......... 606/34 |
| 2006/0281360 A1 | 12/2006 | Sartor et al. |
| 2006/0291178 A1 | 12/2006 | Shih |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |

| | | | | | |
|---|---|---|---|---|---|
| 2007/0208339 A1 | 9/2007 | Arts et al. | EP | 1810633 | 7/2007 |
| 2007/0225698 A1 | 9/2007 | Orszulak et al. | EP | 1854423 | 11/2007 |
| 2007/0250052 A1 | 10/2007 | Wham | FR | 1275415 | 10/1961 |
| 2007/0265612 A1 | 11/2007 | Behnke et al. | FR | 1347865 | 11/1963 |
| 2007/0282320 A1 | 12/2007 | Buysse et al. | FR | 2313708 | 12/1976 |
| 2008/0015563 A1 | 1/2008 | Hoey et al. | FR | 2364461 | 7/1978 |
| 2008/0015564 A1 | 1/2008 | Wham et al. | FR | 2502935 | 10/1982 |
| 2008/0039831 A1 | 2/2008 | Odom et al. | FR | 2517953 | 6/1983 |
| 2008/0039836 A1 | 2/2008 | Odom et al. | FR | 2573301 | 5/1986 |
| 2008/0082094 A1 | 4/2008 | McPherson et al. | GB | 607850 | 9/1948 |
| 2008/0125767 A1 | 5/2008 | Blaha | GB | 702510 | 1/1954 |
| 2008/0177199 A1 | 7/2008 | Podhajsky | GB | 855459 | 11/1960 |
| 2008/0248685 A1 | 10/2008 | Sartor et al. | GB | 902775 | 8/1962 |
| 2008/0281315 A1 | 11/2008 | Gines | GB | 2164473 | 3/1986 |
| 2008/0281316 A1 | 11/2008 | Carlton et al. | GB | 2214430 | 9/1989 |
| 2008/0287791 A1 | 11/2008 | Orszulak et al. | GB | 2358934 | 8/2001 |
| 2008/0287838 A1 | 11/2008 | Orszulak et al. | SU | 166452 | 1/1965 |
| 2009/0018536 A1 | 1/2009 | Behnke | SU | 727201 | 4/1980 |
| 2009/0024120 A1 | 1/2009 | Sartor | WO | WO92/06642 | 4/1992 |
| 2009/0036883 A1 | 2/2009 | Behnke | WO | WO93/24066 | 12/1993 |
| 2009/0069801 A1 | 3/2009 | Jensen et al. | WO | WO94/24949 | 11/1994 |
| 2009/0082765 A1 | 3/2009 | Collins et al. | WO | WO94/28809 | 12/1994 |
| 2009/0157071 A1 | 6/2009 | Wham et al. | WO | WO95/09577 | 4/1995 |
| 2009/0157072 A1 | 6/2009 | Wham et al. | WO | WO95/19148 | 7/1995 |
| 2009/0157073 A1 | 6/2009 | Orszulak | WO | WO95/25471 | 9/1995 |
| 2009/0157075 A1 | 6/2009 | Wham et al. | WO | WO96/02180 | 2/1996 |
| | | | WO | WO96/04860 | 2/1996 |
| FOREIGN PATENT DOCUMENTS | | | WO | WO96/08794 | 3/1996 |
| DE | 1139927 | 11/1962 | WO | WO96/18349 | 6/1996 |
| DE | 1149832 | 6/1963 | WO | WO96/29946 | 10/1996 |
| DE | 1439302 | 1/1969 | WO | WO96/39086 | 12/1996 |
| DE | 2439587 | 2/1975 | WO | WO96/39914 | 12/1996 |
| DE | 2455174 | 5/1975 | WO | WO97/06739 | 2/1997 |
| DE | 2407559 | 8/1975 | WO | WO97/06740 | 2/1997 |
| DE | 2602517 | 7/1976 | WO | WO97/06855 | 2/1997 |
| DE | 2504280 | 8/1976 | WO | WO97/11648 | 4/1997 |
| DE | 2540968 | 3/1977 | WO | WO97/17029 | 5/1997 |
| DE | 2820908 | 11/1978 | WO | WO98/07378 | 2/1998 |
| DE | 2803275 | 8/1979 | WO | WO98/18395 | 5/1998 |
| DE | 2823291 | 11/1979 | WO | WO98/27880 | 7/1998 |
| DE | 2946728 | 5/1981 | WO | WO99/12607 | 3/1999 |
| DE | 3143421 | 5/1982 | WO | WO02/00129 | 1/2002 |
| DE | 3045996 | 7/1982 | WO | WO02/11634 | 2/2002 |
| DE | 3120102 | 12/1982 | WO | WO02/45589 | 6/2002 |
| DE | 3510586 | 10/1986 | WO | WO02/47565 | 6/2002 |
| DE | 3604823 | 8/1987 | WO | WO02/053048 | 7/2002 |
| DE | 390937 | 4/1989 | WO | WO02/088128 | 7/2002 |
| DE | 3904558 | 8/1990 | WO | WO03/090630 | 11/2003 |
| DE | 3942998 | 7/1991 | WO | WO03/090635 | 11/2003 |
| DE | 4339049 | 5/1995 | WO | WO03/092520 | 11/2003 |
| DE | 19717411 | 11/1998 | WO | WO2004/028385 | 4/2004 |
| DE | 19848540 | 5/2000 | WO | WO2004/098385 | 4/2004 |
| EP | 246350 | 11/1987 | WO | WO2004/043240 | 5/2004 |
| EP | 310431 | 4/1989 | WO | WO 2004043240 | 5/2004 |
| EP | 325456 | 7/1989 | WO | WO2004043240 A | 5/2004 |
| EP | 336742 | 10/1989 | WO | WO2004/052182 | 6/2004 |
| EP | 390937 | 10/1990 | WO | WO2004/103156 | 12/2004 |
| EP | 556705 | 8/1993 | WO | WO2005/046496 | 5/2005 |
| EP | 569130 | 11/1993 | WO | WO2005/048809 | 6/2005 |
| EP | 608609 | 8/1994 | WO | WO2005/050151 | 6/2005 |
| EP | 694291 | 1/1996 | WO | WO2005/060365 | 7/2005 |
| EP | 836868 | 4/1998 | WO | WO2005/060849 | 7/2005 |
| EP | 878169 | 11/1998 | WO | WO2006/050888 | 5/2006 |
| EP | 1051948 | 11/2000 | WO | WO 2006050888 | 5/2006 |
| EP | 1053720 | 11/2000 | WO | WO2006050888 A | 5/2006 |
| EP | 1151725 | 11/2001 | WO | WO2006/105121 | 10/2006 |
| EP | 1293171 | 3/2003 | | | |
| EP | 1472984 | 11/2004 | OTHER PUBLICATIONS | | |
| EP | 1495712 | 1/2005 | | | |
| EP | 1500378 | 1/2005 | | | |
| EP | 1535581 | 6/2005 | | | |
| EP | 1609430 | 12/2005 | | | |
| EP | 1707144 | 3/2006 | | | |
| EP | 1645235 | 4/2006 | | | |
| EP | 880220 | 6/2006 | | | |
| EP | 1707143 | 10/2006 | | | |
| EP | 1744354 | 1/2007 | | | |
| EP | 1810628 | 7/2007 | | | |
| EP | 1810630 | 7/2007 | | | |

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Anderson et al., "A Numerical Study of Rapid Heating for High Temperature Radio Frequency Hyperthermia" International Journal of Bio-Medical Computing, 35 (1994) pp. 297-307.

Astrahan, "A Localized Current Field Hyperthermia System for Use with 192-Iridium Interstitial Implants" Medical Physics, 9 (3), May/Jun. 1982.

Bergdahl et al., "Studies on Coagulation and the Development of an Automatic Computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedance" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation-'COA-COMP'" Neurosurgical Review 7:2-3 (1984) pp. 187-190.
Wald et al., "Accidental Burns",JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(March 2005); pp. 160-164.
Muller et al. "Extended Left Hemicolectomy Using the LigaSure Vessel Sealing System" Innovations That Work; Sep. 1999.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3.dated Dec. 28, 2005.
International Search Report EP 05021944.3 dated Jan. 18, 2006.
International Search Report EP 05022350.2 dated Jan. 18, 2006.
International Search Report EP 05002769.7 dated Jun. 9, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001527.6 dated May 9, 2007.
International Search Report EP 07004355.9 dated May 21, 2007.
International Search Report EP 07008207.8 dated Sep. 5, 2007.
International Search Report EP 07010673.7 dated Sep. 24, 2007.
US 6,878,148, 04/2005, Goble et al. (withdrawn).
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
International Search Report EP04707738 dated Jul. 4, 2007.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/USO4/02961 dated Aug. 2, 2005.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.

* cited by examiner

REAL-TIME ARC CONTROL IN ELECTROSURGICAL GENERATORS

BACKGROUND

1. Technical Field

The present disclosure relates to electrosurgical apparatuses, systems and methods. More particularly, the present disclosure is directed to electrosurgical generators configured to control energy output on a per arc basis. The generator detects aberrations within continuous or pulsed waveforms indicative of sudden changes in the current. In particular the generator monitors for deviations from the sinusoidal or pulsed sinusoidal current waveforms as compared to the voltage waveform.

2. Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current to a surgical site to cut, ablate, coagulate or seal tissue. In monopolar electrosurgery, an active electrode delivers radio frequency energy from the electrosurgical generator to the tissue and a return electrode carries the current back to the generator. In monopolar electrosurgery, the active electrode is typically part of the surgical instrument held by the surgeon and applied to the tissue to be treated. A patient return electrode is placed remotely from the active electrode to carry the current back to the generator.

Ablation is most commonly a monopolar procedure that is particularly useful in the field of cancer treatment, where one or more RF ablation needle electrodes (usually having elongated cylindrical geometry) are inserted into a living body and placed in the tumor region of an affected organ. A typical form of such needle electrodes incorporates an insulated sheath from which an exposed (uninsulated) tip extends. When an RF energy is provided between the return electrode and the inserted ablation electrode, RF current flows from the needle electrode through the body. Typically, the current density is very high near the tip of the needle electrode, which tends to heat and destroy surrounding issue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned immediately adjacent the electrodes. When the electrodes are sufficiently separated from one another, the electrical circuit is open and thus inadvertent contact with body tissue with either of the separated electrodes does not cause current to flow.

During electrosurgical procedures, the magnitude and temporal characteristics of the voltage and current as supplied by the electrosurgical generator determine energy density pathways and tissue temperatures. This may be accomplished by keeping the total delivered power constant while varying other energy properties, such as voltage, current, etc. These configurations are not configured for detecting and controlling arcing conditions between the active electrode and tissue. It is particularly desirable to prevent the occurrence of uncontrolled electrical arcs and concomitant energy deposition on a half cycle or shorter time scale, in order to avoid inadvertent tissue damage and to achieve optimum conditions. Thus, there is a continual need for electrosurgical generators which are configured to sense tissue and energy properties to determine arcing conditions and control energy output based on these determinations.

SUMMARY

According to one aspect of the present disclosure, an electrosurgical generator is disclosed. The generator includes a radio frequency output stage configured to generate a radio frequency waveform and a sensor circuit configured to measure a property of the radio frequency waveform during a predetermined sampling period. The generator also includes a controller configured to determine a total charge transported and/or total energy deposited by the radio frequency waveform during the predetermined sampling period to determine an arc event. In particular the arc duration of special interest as determined by the deviation of the current and voltage waveforms, as well as the integral of this difference to determine the total change in the arc. Arcing can be characterized by an uncontrolled disparity between the voltage and current waveforms with the current waveform being much larger for a short period compared to the characteristic waveforms. The controller is further configured to adjust the output of the electrosurgical generator based on at least one parameter associated with the arc event.

A method for operating an electrosurgical generator is also contemplated by the present disclosure. The method includes the steps of selecting duration of sampling period, measuring voltage and current of a radio frequency waveform having a current waveform and a voltage waveform across a series resistor of the electrosurgical generator during the sampling period and temporally integrating voltage across the series resistor to determine total charge deposited into tissue by the radio frequency waveform during the sampling period and in particular during the arc duration. The method also includes the steps of temporally integrating power of the at least one radio frequency waveform during the sampling period to determine total energy deposited into tissue by the radio frequency waveform during the sampling period, by isolating the interval during which the current waveform is different from the voltage waveform to determine energy per arc event as a function of the total charge and total energy delivered and determining the amount of energy to be deposited into tissue per arc event.

According to a further embodiment of the present disclosure, an electrosurgical generator is disclosed. The electrosurgical generator includes a radio frequency output stage configured to generate a radio frequency waveform having a current waveform and a voltage waveform, a sensor circuit configured to measure voltage and current of a radio frequency waveform during a predetermined sampling period, and a controller configured to compare the voltage waveform and the current waveform and to provide a signal representative of the comparison. The controller includes a total charge calculator module configured to temporally integrate current of the radio frequency waveform and in particular the current during the interval when the current waveform departs from the voltage waveform to determine the total charge deposited by the radio frequency waveform during the predetermined sampling period as well as during the arc events. The controller also includes a total energy calculator module configured to integrate total power deposited by the radio frequency waveform to determine the total energy deposited by the radio frequency waveform during the predetermined sampling period for the radio frequency waveform and for arc events. The controller is further configured to determine an arc event as a function of the total charge and total energy and to adjust the output of the electrosurgical generator if the arc event is determined to avoid undesired tissue damage by setting a threshold energy above which the arc event is extinguished.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The generator according to the present disclosure can perform monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1A:
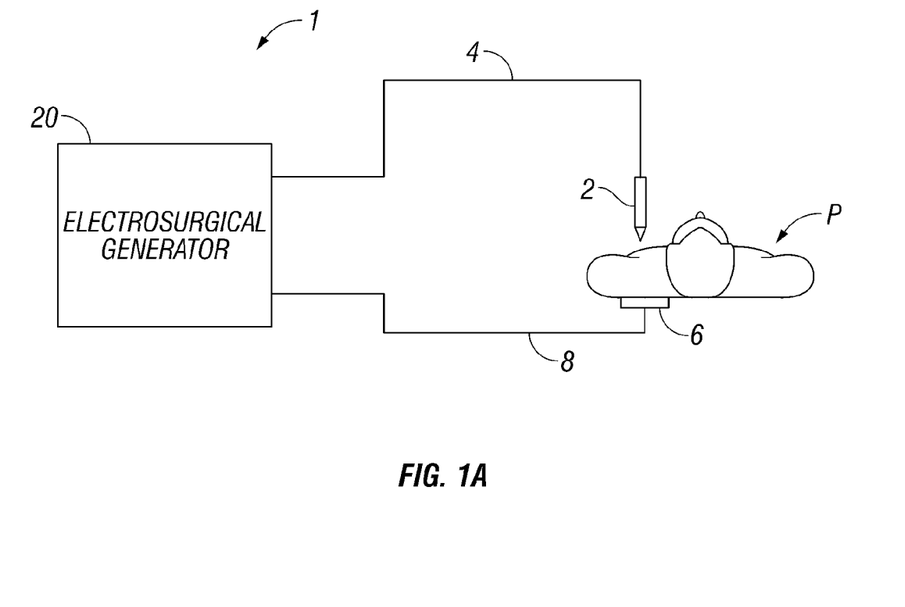
FIGS. 1A-1B are schematic block diagrams of an electrosurgical system according to the present disclosure.

FIG. 1A is a schematic illustration of a monopolar electrosurgical system 1 according to one embodiment of the present disclosure. The system 1 includes an electrosurgical instrument 2 having one or more electrodes for treating tissue of a patient P. The instrument 2 is a monopolar type instrument including one or more active electrodes (e.g., electrosurgical cutting probe, ablation electrode(s), etc.). Electrosurgical RF energy is supplied to the instrument 2 by a generator 20 via a supply line 4, which is connected to an active terminal 30 (FIG. 2) of the generator 20, allowing the instrument 2 to coagulate, seal, ablate and/or otherwise treat tissue. The energy is returned to the generator 20 through a return electrode 6 via a return line 8 at a return terminal 32 (FIG. 2) of the generator 20. The active terminal 30 and the return terminal 32 are connectors configured to interface with plugs (not explicitly shown) of the instrument 2 and the return electrode 6, which are disposed at the ends of the supply line 4 and the return line 8, respectively.

The system 1 may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage. In one embodiment, the active electrode 6 may be used to operate in a liquid environment, wherein the tissue is submerged in an electrolyte solution.

Figure 1B:
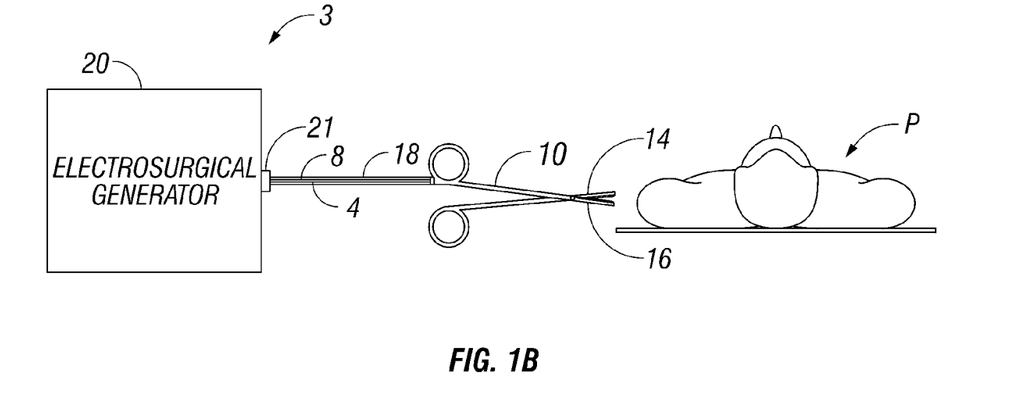
Figure 2:
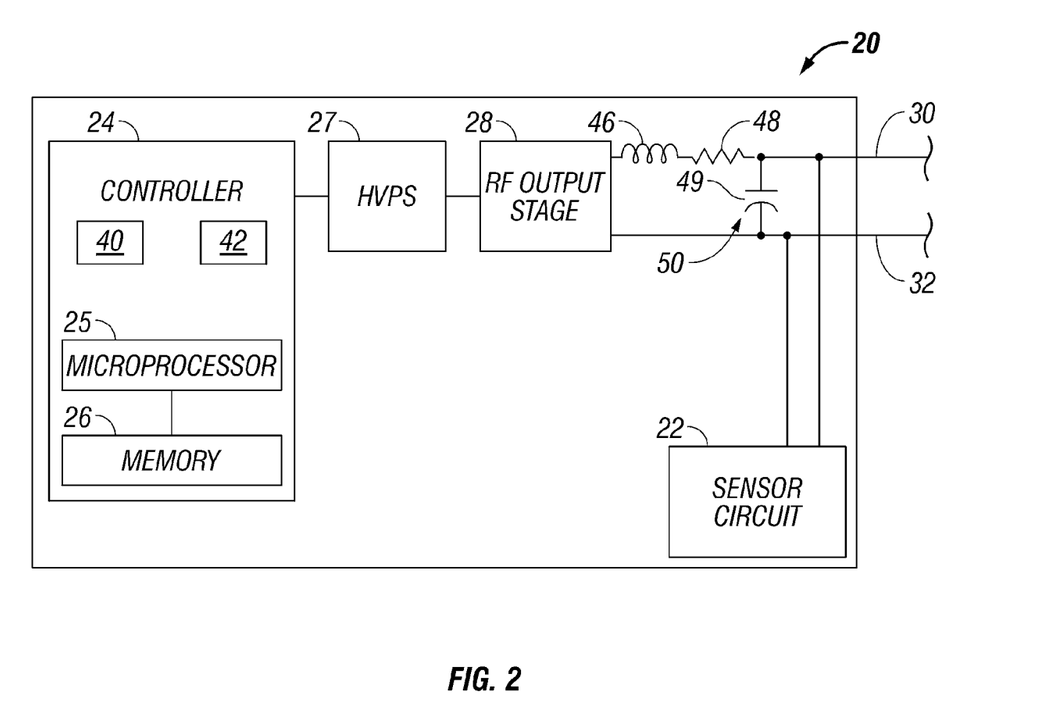
FIG. 2 is a schematic block diagram of a generator according to one embodiment of the present disclosure.

FIG. 1B is a schematic illustration of a bipolar electrosurgical system 3 according to the present disclosure. The system 3 includes a bipolar electrosurgical forceps 10 having one or more electrodes for treating tissue of a patient P. The electrosurgical forceps 10 include opposing jaw members having an active electrode 14 and a return electrode 16, respectively, disposed therein. The active electrode 14 and the return electrode 16 are connected to the generator 20 through cable 18, which includes the supply and return lines 4, 8 coupled to the active and return terminals 30, 32, respectively (FIG. 2). The electrosurgical forceps 10 are coupled to the generator 20 at a connector 21 having connections to the active and return terminals 30 and 32 (e.g., pins) via a plug disposed at the end of the cable 18, wherein the plug includes contacts from the supply and return lines 4, 8.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform, as well as the level of maximum arc energy allowed which varies depending on desired tissue effects and other parameters to achieve the desired waveform suitable for a particular task (e.g., coagulating, tissue sealing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

FIG. 2 shows a schematic block diagram of the generator 20 having a controller 24, a high voltage DC power supply 27 ("HVPS") and an RF output stage 28. The HVPS 27 is connected to a conventional AC source (e.g., electrical wall outlet) and provides high voltage DC power to an RF output stage 28, which then converts high voltage DC power into RF energy and delivers the RF energy to the active terminal 30. The energy is returned thereto via the return terminal 32.

In particular, the RF output stage 28 generates either continuous or pulsed sinusoidal waveforms of high RF energy. The RF output stage 28 is configured to generate a plurality of waveforms having various duty cycles, peak voltages, crest factors, and other suitable parameters. Certain types of waveforms are suitable for specific electrosurgical modes. For instance, the RF output stage 28 generates a 100% duty cycle sinusoidal waveform in cut mode, which is best suited for ablating, fusing and dissecting tissue and a 1-25% duty cycle waveform in coagulation mode, which is best used for cauterizing tissue to stop bleeding.

The radio frequency waveforms include a current and a voltage waveform. The present disclosure provides for a system and method which monitors and compares the voltage and current waveform to detect discrepancies between the waveform on a time scale substantially equal to one-half radio frequency cycle of the waveform.

The generator 20 may include a plurality of connectors to accommodate various types of electrosurgical instruments (e.g., instrument 2, electrosurgical forceps 10, etc.). Further, the generator 20 may operate in monopolar or bipolar modes by including a switching mechanism (e.g., relays) to switch the supply of RF energy between the connectors, such that, for instance, when the instrument 2 is connected to the generator 20, only the monopolar plug receives RF energy.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 allowing the microprocessor 25 to control the output of the generator 20 according to either open and/or closed control loop schemes. Those skilled in the art will appreciate that the microprocessor 25 may be substituted by any logic processor or analog circuitry (e.g., control circuit) adapted to perform the calculations discussed herein.

The generator 20 may implement a closed and/or open loop control schemes which include a sensor circuit 22 having a plurality of sensors measuring a variety of tissue and energy properties (e.g., tissue impedance, tissue temperature, output current and/or voltage, etc.), and providing feedback to the controller 24. A current sensor can be disposed at either the active or return current path or both and voltage can be sensed at the active electrode(s). The controller 24 compares voltage and current waveforms to identify arc events, the duration thereof and total energy of the arc event. The controller 24 then transmits appropriate signals to the HVPS 27 and/or RF output stage 28, which then adjust DC and/or RF power supply, respectively by using a maximum allowable arc energy which varies according to the selected mode. The controller 24 also receives input signals from the input controls of the generator 20 or the instrument 2. The controller 24 utilizes the input signals to adjust power output by the generator 20 and/or performs other control functions thereon.

The sensor circuit 22 measures the electrical current (I) and voltage (V) supplied by the RF output stage 28 in real time to characterize the electrosurgical process during both the matching sinusoidal and non-sinusoidal durations for a predetermined sampling period, the former being of short duration (e.g., half a cycle) and the latter being of long duration (e.g., 15 cycles). This allows for the measured electrical properties to be used as dynamic input control variables to achieve feedback control. The current and voltage values may also be used to derive other electrical parameters, such as power (P=V*I) and impedance (Z=V/I). The sensor circuit 22 also measures properties of the current and voltage waveforms and determines the shape thereof.

More specifically, the controller 20 includes a total charge calculator module 40 and a total energy calculator 42. The total charge calculator module 40 is configured to determine the total charge, "q," delivered to the tissue in Coulombs both on average and during an arc event. This is accomplished by integrating the measured current over the two predetermined sampling periods, the sinusoidal and non-sinusoidal durations. The total energy calculator module 42 determines the total energy, "E," delivered into the tissue during treatment. The total energy calculator module 42 determines the power delivered by generator 20 and then integrates the power over the sampling period. The sampling period can range from about a small fraction of the half-cycle of the electrosurgical waveform during arcs to a plurality of full cycles.

The controller 20 is also configured to determine deviations between one or more properties of the voltage waveform and the current waveform by comparing the waveforms. As stated above, a discrepancy between the voltage and current waveforms is indicative of an arc event, this allows the controller 20 to determine when an arc event has occurred and then utilize the calculators 40 and 42 to determine the total charge, total energy and duration of the arc event. In other words, once an arc even has been detected based on the comparison of the waveforms, the controller 20 thereafter generates a comparison signal and performs total charge and energy calculations for the period of time corresponding to the deviation (e.g., the arc event).

The generator 20 also includes a circuit 50, having a series inductance, a series resistance and a shunt capacitance which are shown schematically as a series inductor 46, a series resistor 48 and a shunt capacitor 49. The inductor 46 and resistor 48 are disposed on the active terminal 30, with the capacitor 49 being disposed between the active and return terminals 30 and 32. Inductance and capacitance of these components is determined by characteristics of the load elements (e.g., the active electrode 2, and the tissue). The resistance is selected for a so-called quality factor, "Q," corresponding to the excitation of the circuit 50. The resistance, inductance and capacitance are also selected to accommodate system and parasitic electrical properties associated with the generator 20 (e.g., inductance and capacitance of the cable 4).

The total charge calculator module 40 determines the total charge, "q," by temporal integration of the voltage across the resistor 48. The charge arises from the stored energy in reactive components described above and available for the arc duration when this energy is suddenly discharged. The sensor circuit 22 measures the voltage at the resistor 48 for the desired sampling period and compares the voltage to the current waveform. The sensor circuit 22 then transmits the voltage, current and time values of the sampling period to the total charge calculator module 40, which thereafter integrates the values to obtain "q." The total energy calculator module 42 determines the total energy, "E," by temporal integration of the product of "q" and the voltage across the capacitor 49 during an arc event. In particular, the controller 24 is configured to utilize the results of the determinations by the total charge calculator module 40 and the total energy calculator module 42 to adjust the operation of the generator 20 during the arc-free and arc events. For every detected arc event, the controller 24 is configured to set a maximum energy to be delivered by the RF output stage 28 per instantaneous arc based on formula (1):

$$E = CV^2/2 + LI^2/2 \qquad (1)$$

In formula (1), E is the desired energy, C is the capacitance of the capacitor 49, L is the inductance of the inductor 46, and V is voltage measured across thereof.

In another embodiment, arcing maybe controlled by placing limits on operational parameters in conjunction or in lieu of active feedback control. The limits are based on media properties (e.g., liquid medium in which the tissue is submerged) and mobile charge (e.g., electrolyte) concentrations. Mobile charges in the media can be either positive or negative. Further, the charges move through the media at a different rate defined in units of velocity per electric field. During ideal operation the balance between the positive and negative charges can be expressed by the formula (2):

$$\text{(mobility of negative charges)*(positive voltage magnitude)*(duration of positive voltage)=(mobility of positive species)*(negative voltage magnitude)*(duration of negative voltage)} \qquad (2)$$

The equilibrium between the charges occurs when positive and negative charges travel the same distance, such that there is no accumulation of the faster-moving charges at the surface of the active electrode. Accumulation of faster species at the instance when the voltage switches polarity results in deleteriously high charge density at the tip of the active electrode. The spatial gradient of the charge density gives rise to a potential that is high enough to cause a breakdown which results in arcing. Thus, arcing can be minimized by putting limits on operational parameters of the generator 20 to produce desired waveforms which match or equalize charge transport of each polarity of species. Namely, the voltage, current, and other output parameters of the generator 20 are adjusted as a function of the formula (2) based on prior empirical measurements or experience to decrease the amount of faster charges at the tip of the active electrode when the voltage switches polarity.

Figure 3:
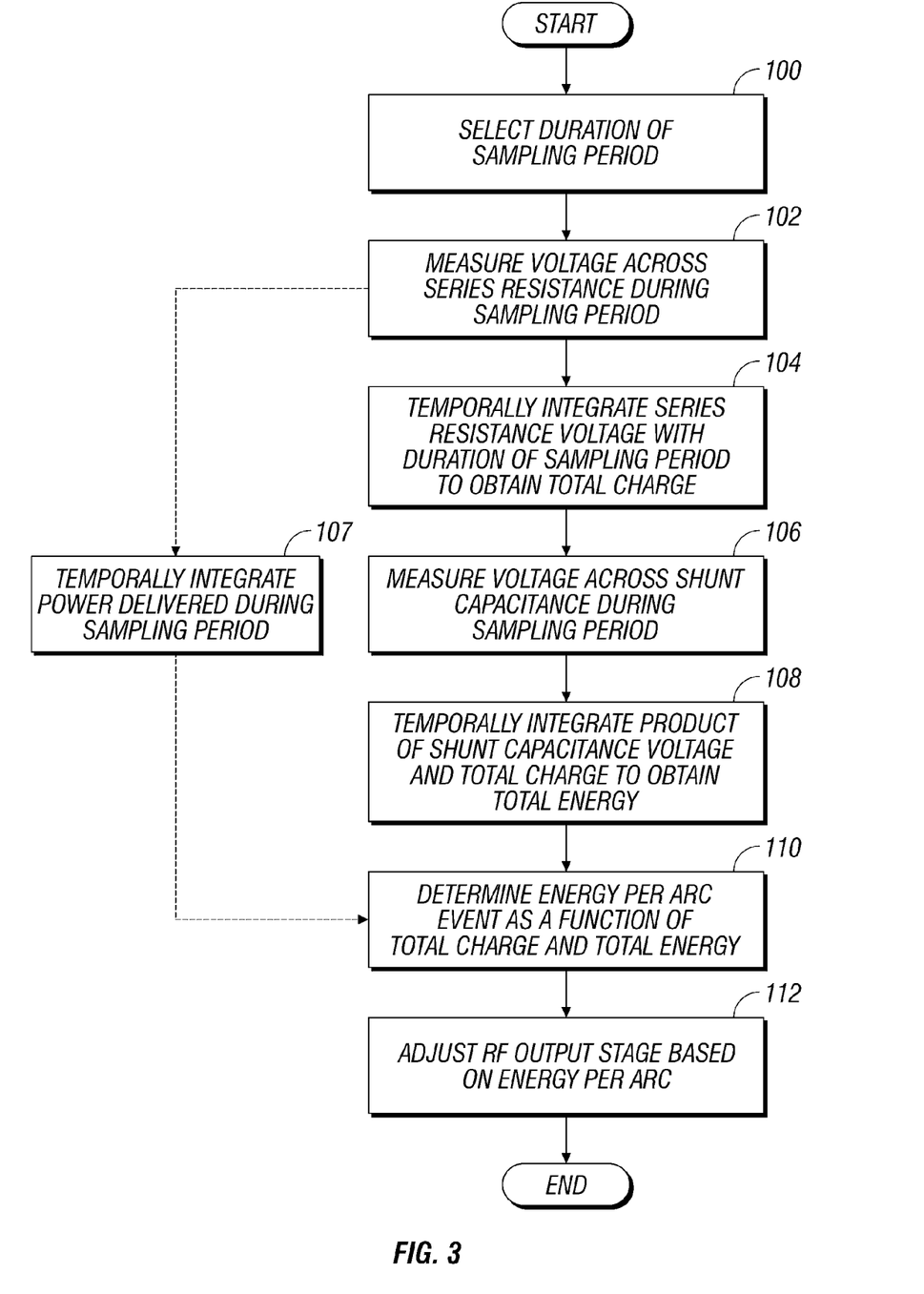
FIG. 3 is a flow chart illustrating a method for determining energy of a radio frequency waveform and arc events thereof according to the present disclosure.

FIG. 3 illustrates a method for adjusting energy per arc in response to total charge and total energy values for arc events and arc-free intervals. In step 100, the controller 24 selects duration for the sampling period, during which the sense circuit 20 is going to measure voltage, current, and other tissue and/or waveform properties. The length of the sampling period can be for the duration of a sub-cycle (e.g., half-cycle) or a plurality of cycles of the waveform, depending on the desired breadth of the value.

In step 102, the sensor circuit 22 measures the voltage across the resistor 48 for the duration of the sampling period. In step 104, the total charge calculator module 40 determines the total charge deposited into the tissue by temporally integrating the current arc waveform at the resistor 48 with respect to the length of the sampling period and deviating from the voltage waveform's sinusoidal character. In addition to the total charge determination, the controller 24 also determines the total energy deposited during the sampling period of the short duration arc. This is accomplished in step 106 by measuring the voltage across the capacitor 49 during the sampling period and comparing the voltage waveform with the current waveform deviations to determine the duration of any arc event and the energy delivered by the arc. In particular, the controller 24 compares the shape of the voltage waveform and the current waveform to determine a deviation between the shape of the voltage waveform and the current waveform indicative of an arc event. In step 108, the total energy calculator module 42 multiplies the shunt capacitance voltage and the total charge calculated in step 104 to determine total energy.

In another embodiment, as illustrated in step 107, the total energy calculator module 42 determines the total energy amount in both the arc free duration and during the arc event by determining the power supplied to the tissue and thereafter temporally integrating the power value deposited to the tissue during the sampling period. In step 110, the controller 24 determines a desired amount of energy to be deposited into tissue per arc event by using the formula (1). In step 112, the controller 24 signals the RF output stage 28 to output the desired energy level on a per arc basis. This allows the generator 20 to tailor the output to avoid arcing beyond a predetermined set point depending on the selected electrosurgical mode. Thus, as an arcing event is detected, the output is adjusted accordingly to avoid tissue damage.

In embodiments, steps 102 and 104 can run concurrently with steps 106 and 108, such that total charge and total energy calculations are performed simultaneously and the output of these calculations are provided in parallel to the controller 24 in step 110.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator comprising:
    a radio frequency output stage configured to generate at least one radio frequency waveform having a voltage waveform and a current waveform;
    a sensor circuit configured to determine at least one property of each of the voltage waveform and the current waveform during a predetermined sampling period;
    a shunt capacitor disposed between active and return terminals of the electrosurgical generator;
    a controller configured to compare the at least one property of each of the voltage waveform and the current waveform to determine at least one deviation between the at least one property of each of the voltage waveform and the current waveform indicative of an arc event, the controller further configured to determine at least one of total charge, total energy and duration of the arc event based on the at least one deviation, wherein the controller includes a total energy calculator module configured to temporally integrate a product of total charge deposited by the at least one radio frequency waveform and voltage across the shunt capacitor to determine the total energy deposited by the at least one radio frequency waveform during the predetermined sampling period.

2. An electrosurgical generator according to claim 1, wherein the controller is further configured to adjust the output of the electrosurgical generator based on the at least one deviation.

3. An electrosurgical generator according to claim 2, wherein the controller includes a total charge calculator module configured to temporally integrate the voltage waveform to determine the total charge deposited by the at least one radio frequency waveform during the predetermined sampling period.

4. An electrosurgical generator according to claim 2, wherein the total energy calculator is further module configured to temporally integrate total power deposited by the at least one radio frequency waveform to determine the total energy deposited by the at least one radio frequency waveform during the predetermined sampling period.

5. An electrosurgical generator according to claim 1, further comprising:
    a resistor and an inductor coupled in series with the active terminal.

6. An electrosurgical generator according to claim 5, wherein the controller is configured to determine a desired amount of energy to be deposited into tissue per arc event based on a formula $E=CV^2/2+LI^2/2$, wherein E is the desired energy, C is capacitance of the shunt capacitor, L is inductance of a series inductor, I is current and V is voltage measured across the shunt capacitor.

7. A method for operating an electrosurgical generator, comprising the steps of:
    generating at least one radio frequency waveform having a voltage waveform and a current waveform;
    determining at least one property of each of the voltage waveform and the current waveform during a predetermined sampling period;
    measuring amplitude of the voltage waveform across a series resistor of the electrosurgical generator during the sampling period;
    comparing the at least one property of each of the voltage waveform and the current waveform to determine at least one deviation between the at least one property of each of the voltage waveform and the current waveform indicative of an arc event;
    determining at least one of total charge, total energy and duration of the arc event based on the at least one deviation;
    measuring voltage across a shunt capacitor disposed between active and return terminals of the electrosurgical generator during the sampling period; and
    temporally integrating a product of the total charge and the voltage across the shunt capacitor to determine total energy deposited into tissue by the at least one radio frequency waveform during the sampling period.

8. A method according to claim 7, further comprising the steps of:

temporally integrating voltage across the series resistor to determine total charge deposited into tissue by the at least one radio frequency waveform during the sampling period; and temporally integrating power of the at least one radio frequency waveform during the sampling period to determine total energy deposited into tissue by the at least one radio frequency waveform during the sampling period.

9. A method according to claim 7, further comprising the steps of:

calculating a desired maximum amount of energy to be deposited into tissue per arc event to limit the arc event; and adjusting output of the electrosurgical generator based on the desired maximum amount of energy to be deposited into tissue per arc event.

10. A method according to claim 9, wherein the step of calculating the desired maximum amount of energy is based on a formula $E=CV^2/2+LI^2/2$, wherein E is the desired energy, C is capacitance of the shunt capacitor, L is inductance of a series inductor, I is current and V is voltage measured across the shunt capacitor.

* * * * *